(12) United States Patent
Wolfe et al.

(10) Patent No.: US 11,547,812 B2
(45) Date of Patent: Jan. 10, 2023

(54) COMBINED INFUSION SET AND SENSOR

(71) Applicant: PercuSense, Inc., Valencia, CA (US)

(72) Inventors: Katherine Wolfe, Dunwoody, GA (US); Rajiv Shah, Rancho Palos Verdes, CA (US)

(73) Assignee: PercuSense, Inc., Valencia, CA (US)

( * ) Notice: Subject to any disclaimer, the term of this patent is extended or adjusted under 35 U.S.C. 154(b) by 0 days.

(21) Appl. No.: 16/936,754

(22) Filed: Jul. 23, 2020

(65) Prior Publication Data

US 2021/0023313 A1 Jan. 28, 2021

Related U.S. Application Data

(60) Provisional application No. 62/877,371, filed on Jul. 23, 2019.

(51) Int. Cl.
  *A61M 5/46* (2006.01)
  *A61M 5/172* (2006.01)
  *A61M 5/142* (2006.01)

(52) U.S. Cl.
  CPC .......... *A61M 5/46* (2013.01); *A61M 5/14244* (2013.01); *A61M 5/1723* (2013.01); *A61M 2205/3327* (2013.01)

(58) Field of Classification Search
  CPC .. A61M 5/46; A61M 5/14244; A61M 5/1723; A61M 2205/3327; A61M 2005/14252; A61M 5/329; A61M 5/14; A61M 5/168; A61M 5/142; A61M 2005/1726; A61M 25/0102; A61M 17/3494; A61B 5/6848; A61B 5/6849; A61B 5/14865; A61B 5/1473; A61B 5/1459; A61B 5/14503; A61B 17/3494
  See application file for complete search history.

(56) References Cited

U.S. PATENT DOCUMENTS

| | | | | |
|---|---|---|---|---|
| 5,299,571 A | * | 4/1994 | Mastrototaro | ..... A61B 5/14532 600/347 |
| 5,568,806 A | * | 10/1996 | Cheney, II | ........... A61B 5/6849 600/373 |
| 2016/0008028 A9 | * | 1/2016 | Matsumoto | ............ A61B 5/076 600/302 |
| 2018/0289329 A1 | * | 10/2018 | Momoki | .............. A61B 5/6849 |
| 2019/0231238 A1 | * | 8/2019 | Frey | ................... A61B 5/14503 |

OTHER PUBLICATIONS

Nandivada, Venkat; Enhance Electronic Performance with Epoxy Compounds; Jan. 16, 2013; Design World; p. 5 (Year: 2013).*

* cited by examiner

*Primary Examiner* — Theodore J Stigell
*Assistant Examiner* — Phoebe Anne Staton
(74) *Attorney, Agent, or Firm* — PercuSense, Inc.

(57) ABSTRACT

In one embodiment, an infusion set and sensor assembly delivered within a subject is disclosed. The assembly includes a cannula that is terminated at a cannula opening. The assembly further includes a sharp that is at least partially within the hollow of the cannula. A sensor having a proximal end and a distal end is also included in the assembly. The proximal end of the sensor is held in a fixed location while the distal end is retained with a portion of the cannula. The sensor further includes sensor slack, wherein transitioning the sharp from a first position to a second position simultaneously inserts the cannula and sensor to a desired insertion depth within a subject via a single point of insertion.

7 Claims, 7 Drawing Sheets

COMBINED INFUSION SET AND SENSOR

RELATED APPLICATIONS

This application claims the benefit of U.S. provisional application No. 62/877,371 filed Jul. 23, 2019. The application listed above is hereby incorporated by reference in its entirety for all purposes.

FIELD OF THE INVENTION

The present invention is generally directed to devices that perform both enabling infusing of a fluid beneath the skin of a subject along with in vivo monitoring of at least one physiological parameter such as, but not limited to, perfusion, temperature or concentration of at least one analyte within the subject. In particular, the present invention is directed toward combined infusion sets and minimally invasive sensors in a single device via a single insertion point that enables delivery of an infusion fluids and also provides real-time information regarding the presence or concentration of an analyte or analytes such as, but not limited to, glucose, oxygen or lactate within a subject.

BACKGROUND OF THE INVENTION

Diabetes is a growing healthcare crisis, affecting nearly 30 million people in the United States. Approximately 10 percent of those affected require intensive glucose and insulin management. In hospital patients, hypoglycemia in both diabetic and non-diabetic patients is associated with increased cost and short- and long-term mortality.

To prevent complications, diabetes requires ongoing management. Continuous glucose monitoring (CGM) has been shown in studies to be the most effective way to improve glucose control, whether used with insulin injections or a continuous insulin pump. CGM systems typically rely on sensors that are implanted under the skin for time periods varying between days and weeks. CGM has been optionally incorporated with infusion pump therapy. Used together CGM and an infusion pump enables an artificial pancreas system which have demonstrated improved both short and long term patient outcomes.

However, improvements in care and outcome would ideally not come at the expense of user comfort and convenience. Having to perform an insertion of the CGM sensors and an infusion set can be viewed as a hindrance or encumbrance that dissuade users from adopting an artificial pancreas system. Thus, it could be viewed as advantageous to minimize the number of insertions to enable an artificial pancreas system.

Accordingly, it would be highly advantageous to enable the insertion of a combined infusion set and sensor via a single insertion point. The claimed invention seeks to address many issues associated with single point insertion of a combined infusion set and sensor.

BRIEF SUMMARY OF THE INVENTION

In one embodiment, an infusion set and sensor assembly delivered within a subject is disclosed. The assembly includes a cannula that is terminated at a cannula opening. The assembly further includes a sharp that is at least partially within the hollow of the cannula. A sensor having a proximal end and a distal end is also included in the assembly. The proximal end of the sensor is held in a fixed location while the distal end is retained with a portion of the cannula. The sensor further includes sensor slack, wherein transitioning the sharp from a first position to a second position simultaneously inserts the cannula and sensor to a desired insertion depth within a subject via a single point of insertion.

In another embodiment, a combined infusion set and sensor for placement within tissue is disclosed. The combined infusion set and sensor includes a housing having a base plate that includes a base opening. Also included is a circuit board with a board opening that is at least partially aligned with the base opening. A cannula that is terminated at a cannula opening is also found in the combined infusion set and sensor. A sharp is at least partially within the cannula and the combined infusion set further includes the sensor having a proximal end and distal end. The proximal end is in electrical contact with the circuit board and a distal end is retained or coupled to a portion of the cannula. The sensor further includes sensor slack, and the cannula, the sharp and the sensor are configured to transition from a first position to a second position. During the transition the sharp protrudes through the cannula opening and the transition to the second position eliminates the sensor slack and the second position results in the cannula and sensor being placed within the tissue via a single point of insertion.

Other features and advantages of the invention will become apparent from the following detailed description, taken in conjunction with the accompanying drawings that illustrate, by way of example, various features of embodiments of the invention.

DETAILED DESCRIPTION

Figure 1:
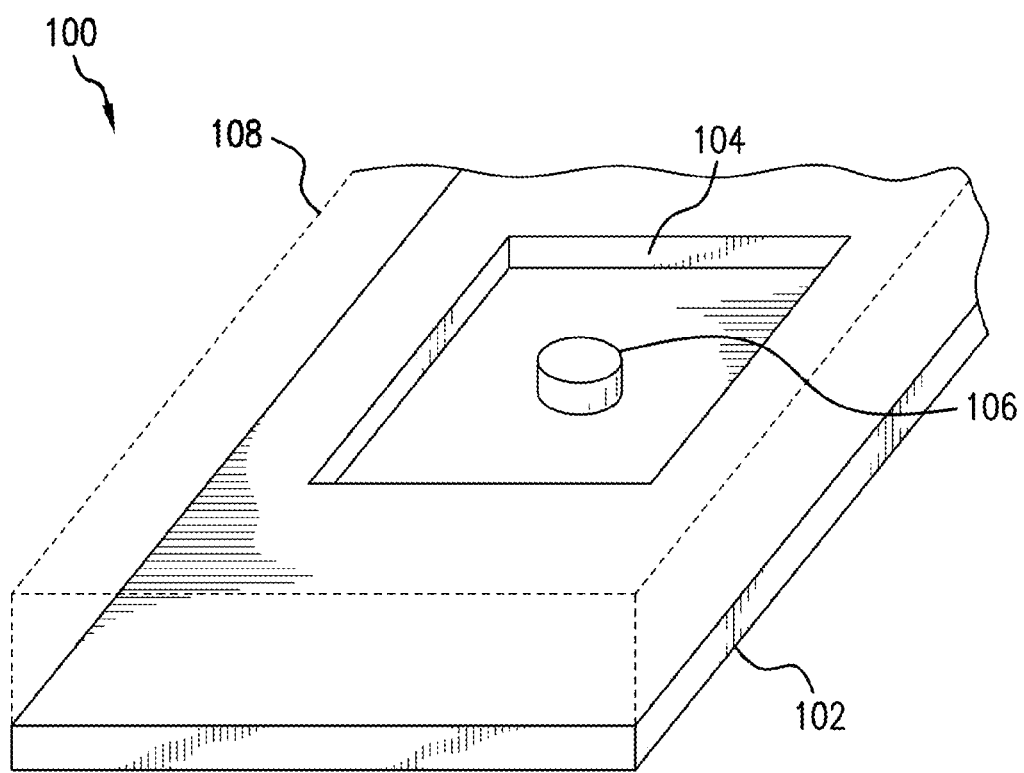
FIG. 1 is a pseudo isometric illustration of some of exemplary basic structural components for a unified assembly that combines an infusion set and sensor assembly, in accordance with embodiments of the present invention.

Presented below are embodiments that are intended to enable a combined infusion set and sensor. The combination of an infusion set and sensor can simplify the use of artificial pancreas systems that require a glucose sensor and infusion set. Simplifying use of an artificial pancreas system can improve adoption rates and promote long term use of the system. In many embodiments the sensor incorporated with the combined infusion set is configured to be flexible. In preferred embodiments the sensor is flexible enough to double back upon itself such as, but not limited to s-shapes or u-shapes without breaking or compromising sensor performance.

The combined infusion set and sensor is not limited to use with artificial pancreas systems. Additional embodiments can include sensors, such as, but not limited to electrochemical sensors configured to measure analytes such as lactate, ketones, reactive oxygen, oxygen and the like. Still other embodiments include sensors that are configured to measure multiple analytes, such as, but not limited to combinations of glucose, lactate, oxygen, reactive oxygen and ketones. Similarly, the infusion set may be configured to deliver infusion fluids other than insulin. In various embodiments the combined infusion set and sensor can be used to infuse fluids such as intravenous fluid or medicinal fluids such as, but not limited to pain medications or liquid nutrition. Likewise, while insulin delivery via infusion is typically delivered within the subcutaneous tissue of a subject, in alternative embodiments the combined infusion set and sensor can be used in systems such as, but not limited to, the venous system, musculature, organs and the like.

In many embodiments the combined infusion set and sensor is placed within a subject using a single sharp. In many embodiments the sharp may be a hollow or solid needle. In other embodiments the sharp may be a lancet or the like. The specific embodiments of sharps disclosed are intended to be exemplary and should not be construed as limiting. Any device capable of piercing the skin of a subject to enable placement of the combined infusion set and sensor should be construed as within the scope of this disclosure.

The various embodiments discussed below should not be viewed as discrete embodiments. Rather, it is intended that various elements or components of the various embodiments are intended to be combined with elements, features or components of the other embodiments. While embodiments and examples may be related to particular figures the scope of the disclosure and claims should not be construed to be limited to the explicit embodiments discussed. Rather it should be recognized that various combinations of features, elements and components can be interchanged, combined and even subtracted to enable other embodiments capable of delivering a combined infusion set and sensor via a single point of insertion capable of assisting in the diagnosis and monitoring of various metabolic conditions or general physiological health.

FIG. 1 is a pseudo isometric illustration of some of exemplary basic structural components for a unified assembly 100 that combines an infusion set and sensor assembly, in accordance with embodiments of the present invention. The exemplary components of the unified assembly 100 illustrated in FIG. 1 include a housing 108 that further includes a base plate 102. The housing 108 encloses the unified assembly and may include a single or plurality of openings to enable fluid or electrical communication through the housing 108. The base plate 102 includes a through hole 106 for a cannula. In many embodiments the base plate 102 further includes a base box 104. In some embodiments the base box 104 is molded into the base plate 102. In other embodiments the base box 104 is a separate plastic assembly that can be secured to the base plate 102. The base box 104, illustrated in FIG. 1 as an open top box, should be construed as capable of taking any shape that can at least partially encompass the through hole 106. The function or purpose of the base box is to provide structure for electrical contacts and to contain or distribute potential fluid leaks from either the fluid being infused or from a wound created during insertion of the unified assembly 100.

Figure 2A:
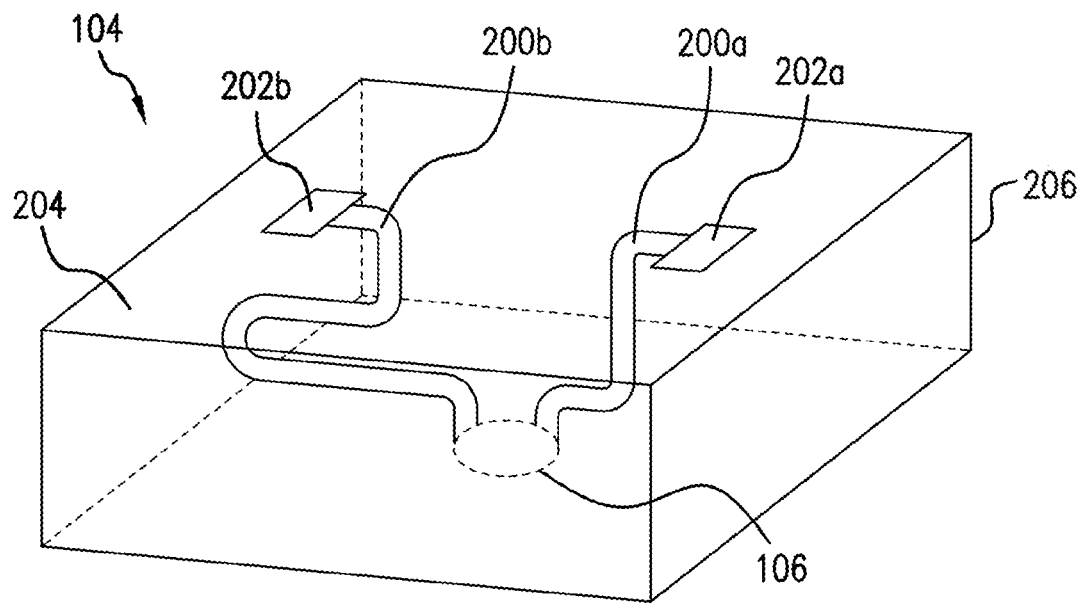
FIGS. 2A and 2B are exemplary illustrations of base boxes that further include sensors, in accordance with embodiments of the present invention.
Figure 2B:
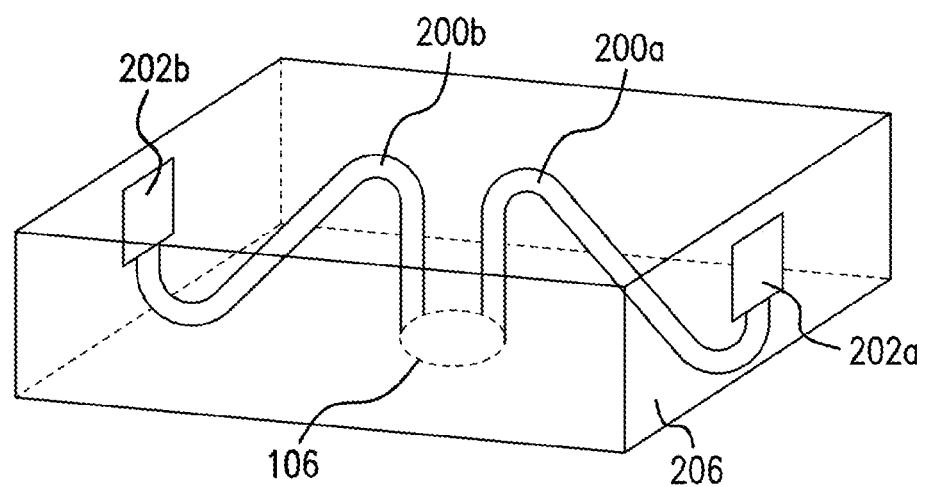

FIGS. 2A and 2B are exemplary illustrations of base boxes 104 that further include sensors 200a and 200b, in accordance with embodiments of the present invention. In many embodiments the sensors 200a and 200b include elements such as, but not limited to, single or multiple working electrodes, counter electrodes, reference electrodes or pseudoreference electrodes. In some embodiments each sensor 200a and sensor 200b are configured as fully functional electrochemical sensors each having a discrete working electrode and a discrete pseudoreference electrode. In this embodiment, the sensors 200a and 200b may be configured to measure the same or different analytes. In other embodiments, the sensor 200a may include one or more working electrodes while the sensor 200b includes a counter electrode and a reference electrode, or even a single or multiple pseudoreference electrodes that operate as both counter electrode and reference electrode to the various working electrodes. In these embodiments, the combination of the sensor 200a and 200b are required to form a functional electrochemical sensor.

In many embodiments the sensors 200a and 200b may have various configurations, such as those discussed in U.S. patent application Ser. No. 15/472,194 filed on Mar. 28, 2017 and Ser. No. 16/152,727 filed on Oct. 5, 2018; along with PCT serial number PCT/US2018/038984 filed on Jun. 22, 2018, which are hereby incorporated by reference for all purposes. In many embodiments, the sensor 200a and 200b are configured to measure real-time concentrations of at least one or more analytes in vivo such as, but not limited to glucose, lactate, ketones, oxygen, reactive oxygen species and the like. In some embodiments the sensors 200a and 200b acquire in vivo measurements of an analyte while placed within at least a physical location on a subject such as, but not limited to, subcutaneous tissue, muscle tissue, intravenously or the like.

Many embodiments of the base box 104 further include contact pads 202a and 202b. For clarity the contact pads 202a and 202b are illustrated as a singular entity. However, in many embodiments the contact pads 202a and 202b may include multiple contacts that electrically interface with elements on the corresponding sensors 200a and 200b. In FIG. 2A the contact pads 202a and 202b are shown on a top 204 surface of the base box 104. In FIG. 2B the contact pads 202a and 202b are shown on a side 206 surface of the base box 104. The embodiments illustrated in FIGS. 2A and 2B should not be construed as limiting as other embodiments can include the contact pad 202a on the side 206 while the contact pad 202b can be on the top 204. Alternatively, in embodiments where the sensor 200a or 200b is independently fully functional, a single sensor 200a or 200b can be connected to a single contact pad on any surface of the base box 104. Additionally, in FIGS. 2A and 2B, portions of the sensors 200a and 200b can be positioned near the through hole 106. The positioning of the sensors 200a and 200b near the through hole 106 enables the sensors 200a and 200b to be mounted into a cannula (not shown) that traverse the base box 104 via the through hole 106.

Figure 3:
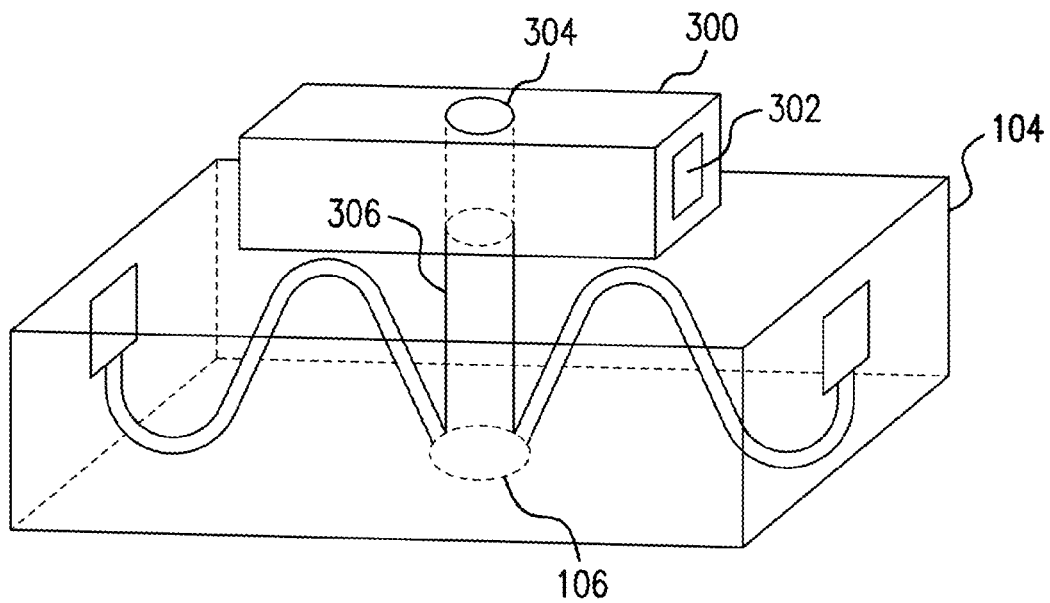
FIG. 3 is an exemplary illustration of a fluid box positioned relative to the base box, in accordance with embodiments of the present invention.

FIG. 3 is an exemplary illustration of a fluid box 300 positioned relative to the base box 104, in accordance with embodiments of the present invention. The fluid box 300 includes a pass through 304 that is configured to accommodate a cannula 306. The cannula 306 is intended to be aligned with the through hole 106 of the base box 104 enabling the cannula to traverse through each of the fluid box 300, the base box 104 and the base plate (not shown) during an insertion process. In many embodiments the pass through 304 includes a self sealing septum. A volume below the self sealing septum is capable of being filled with an infusion fluid when an infusion line is attached to the fluid box 300 via a fluid connector 302.

In many embodiments, during an insertion process the fluid box 300 is displaced from a first position outside of the base box 104 to a second position that secures the fluid box 300 within the base box 104. In preferred embodiments, portions of the sensors within the base box 104 are coupled with the portions of the cannula. Accordingly, during the insertion process portions of the sensor are inserted into a subject as the cannula traverses through the fluid box 300, the base box 104 and the base plate (not shown). During the insertion process, sensor slack, or alternatively an amount of sensor that may be at least partially double backed upon itself, is initially contained within the base box 104 is eliminated as the sensors are placed below the skin of the subject. In other embodiments, rather than completely eliminating sensor slack, there is a change in the amount of sensor slack, or the amount of sensor being at least partially doubled back on itself changes. In many embodiments features formed on either the base box 104 or the fluid box 300 compliment or cooperate with features included on base box 104 and/or the fluid box 300, such as, but not limited to seals and physical pathways that direct or channel fluid entering from the through hole away from electrical contacts or electrical connections.

In some embodiments, portions of the sensor are staked to the cannula. In other embodiments portions of the sensor are coupled to the cannula using other mechanical techniques such as, but not limited to adhesives, friction fit or interference fit, and the like. In some embodiments portions of one or more of the sensors are coupled to the bottom of the fluid box. Coupling techniques between the sensor and the bottom of the fluid box can provide a seal against the base box to facilitate sealing against fluid ingress. Note that coupling the sensors to the cannula can increase rigidity of the cannula as the sensor slack is unfurled along the cannula. The intentional placement of the sensor adjacent to the cannula can result in the cannula being less susceptible to kinking or bending during the insertion process.

Figure 4A:
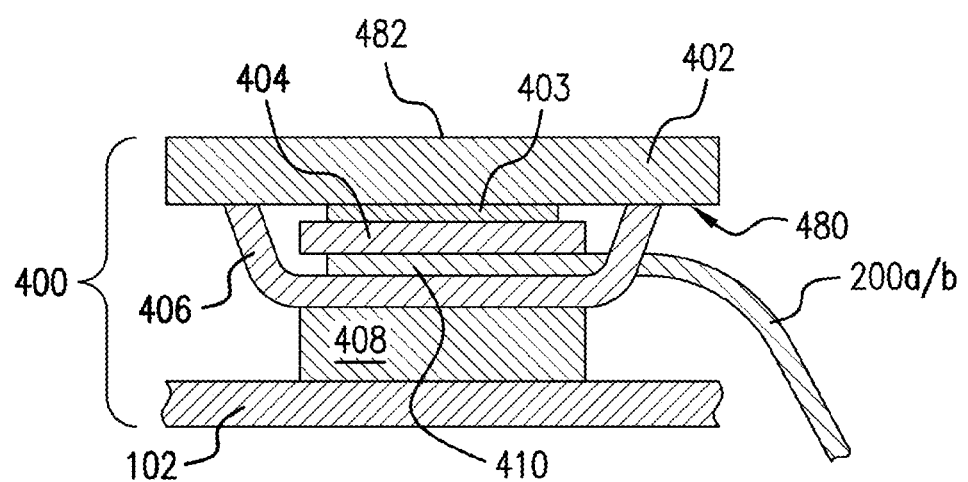
FIG. 4A is an exemplary illustration of a cross-section of a contact stack, in accordance with embodiments of the present invention.

FIG. 4A is an exemplary illustration of a cross-section of a contact stack 400, in accordance with embodiments of the present invention. The contact stack 400 illustrated in FIG. 4A is an exemplary embodiment of how the sensor 200a/b is electrically connected to a contact 403 on a circuit board 402. The illustration in FIG. 4A has the sensor 200a/b adjacent to contact 403 on an underside 480 of the circuit board 402. However, in other embodiments the contact 403 may be located on an upper side 482 and the remainder of the contact stack 400 can be adjusted accordingly to accommodate connection on the upper side 482.

In the contact stack 400 a proximal end 410 of the sensor 200a/b makes electrical contact with contact 403 via a compliant materials 404. In many embodiments the compliant material 404 is a conductive elastomer that accommodates small mechanical movements of the sensor 200a/b such as compression and small shifts of the sensor proximal end 410, without compromising electrical conductivity between the sensor 200a/b and the contact 403. A seal 406 encapsulates the contact 403, the compliant materials 404 and the proximal end 410 while the remainder of the sensor 200a/b passes through the seal 406. In many embodiments the seal 406 is a moisture impermeable flexible adhesive or sealant. In some embodiments the contact stack 400 includes a spacer 408 that locates the contact stack 400 at a preferred distance from the base plate 102. In some embodiments the spacer 408 can be a compliant material intended to reduce or minimize transmission of vibrations from the base plate to the contact stack. In other embodiments the spacer 408 can be a feature such as, but not limited to, a rib or a boss that is molded into the base plate 102. The embodiment illustrated in FIG. 4A can be incorporated into the base box illustrated in FIGS. 1-3 via electrical connections between the circuit board 402 and the contact pads 202a/b.

Figure 4B:
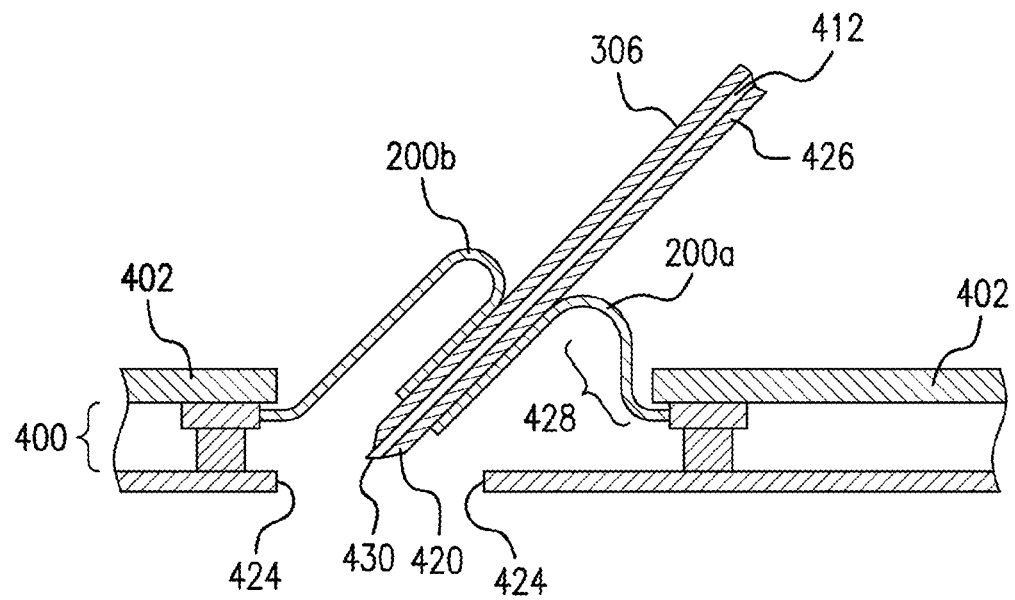
FIG. 4B is an exemplary illustration of a combined infusion set and sensor in a first position prior to insertion, in accordance with embodiments of the present invention.

FIG. 4B is an exemplary illustration of a combined infusion set and sensor in a first position prior to insertion, in accordance with embodiments of the present invention. The first position illustrated in FIG. 4B is intended to be illustrative of the combined infusion set and sensor prior to beginning the insertion process. Accordingly, the components that are intended to be placed under the skin are shown within an opening 424. In many embodiments, the opening 424 is substantially equivalent to the previously discussed opening in the base plate. The components intended to be placed under the skin during the insertion process include the sensors 200a and 200b, the cannula 306 and the sharp 412. In the first position, a portion of the sharp 412 is located within a cannula hollow 426 and a tip 430 of the sharp 412 is within a cannula opening 420.

The sensor 200a is illustrated with sensor slack 428. Note that the sensor slack 428 can also be viewed as an amount of sensor that is doubled back on itself. In some embodiments sensor slack may be defined as the amount of sensor double backed on itself from a fixed point. In many embodiments the sensor slack may be defined as partial or complete doubling back of the sensor upon itself. Additionally, sensor slack may also encompass single or multiple portions of the sensor being partially or completely doubled back upon itself. Sensor 200b also includes sensor slack but for clarity it does not include a callout. In FIG. 4B sensor slack 428 is illustrated as a slight bend in the sensor 200. However, the illustration is intended to be exemplary rather than limiting. In other embodiments sensor slack 428 can include various geometries and configurations such as, but not limited to accordion folding of the sensor, coiling of the sensor and a serpentine path for the sensor. Alternatively, what is referred to as sensor slack 428 can be viewed as sensor material or sensor body that is intended to be substantially displaced into a subject.

In the first position shown in FIG. 4B the distal ends 414 of the sensors 200a and 200b are illustrated being in contact with the cannula 306. In many embodiments, the sensors 200a and 200b are coupled to the cannula 306 using heat staking, adhesives or mechanical properties such as, but not limited to interference or a friction fit within a channel formed in the cannula 306. During the insertion process, as the cannula 306 and sharp 412 are inserted into the subject, the sensor slack 428 is eliminated or taken up by the vertical displacement of the cannula 306. Alternatively, during the insertion process, the sensor slack 428 can be viewed as being unfurled along the cannula. In many embodiments the channel that accommodates the distal end 414 of the sensors 200a and 200b extends along the cannula for at least the anticipated insertion depth. This extended channel accommodates the unfurled portion of the sensor slack 428. Additionally, the placement of the sensor 200a or 200b within the channel can provide additional rigidity to the cannula to prevent buckling or bending of the cannula. Exemplary embodiments of cannulas having channels to accommodate a sensor can be found in U.S. patent application Ser. No. 15/455,115, filed on Mar. 3, 2017 which is hereby incorporated by reference for all purposes.

Figure 4C:
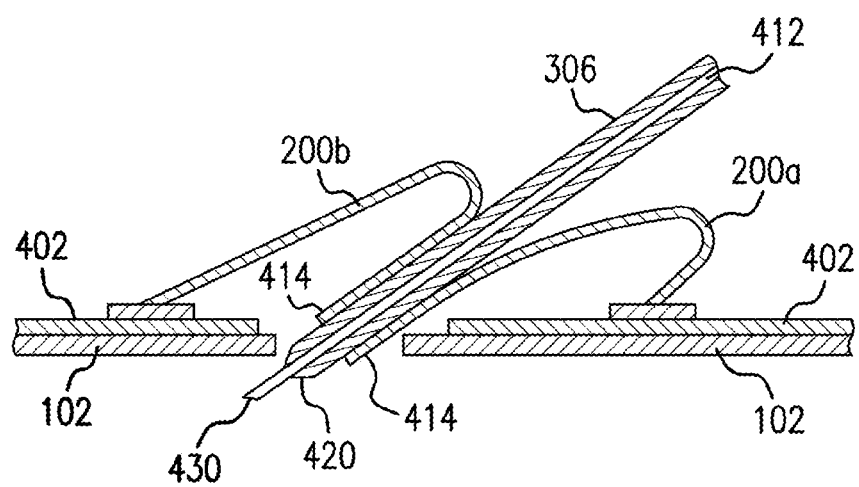
FIG. 4C is an exemplary illustration of a cross-section view of a combined infusion set and sensor in an intermediary position between a first position and a second position, in accordance with embodiments of the present invention.

FIG. 4C is an exemplary illustration of a cross-section view of a combined infusion set and sensor in an intermediary position between a first position and a second position, in accordance with embodiments of the present invention. FIG. 4C is intended to illustrate a moment during the insertion process of the combined infusion set and sensor. The moment being shown is shortly after the initiation of the insertion process where the sharp 412 has moved out of the cannula opening 420, and both the sharp 412 and the cannula 306 have moved below the base opening 424. The embodiment in FIG. 4C differs from FIG. 4B because in FIG. 4B the contact stacks 400 are located on the underside of the circuit board 402 while in FIG. 4C the contact stacks are shown on an upper side of the circuit board 402. In further embodiments, it would be possible to have one contact stack on an upper side of the circuit board while a second contact stack is on an underside of the circuit board.

Figure 4D:
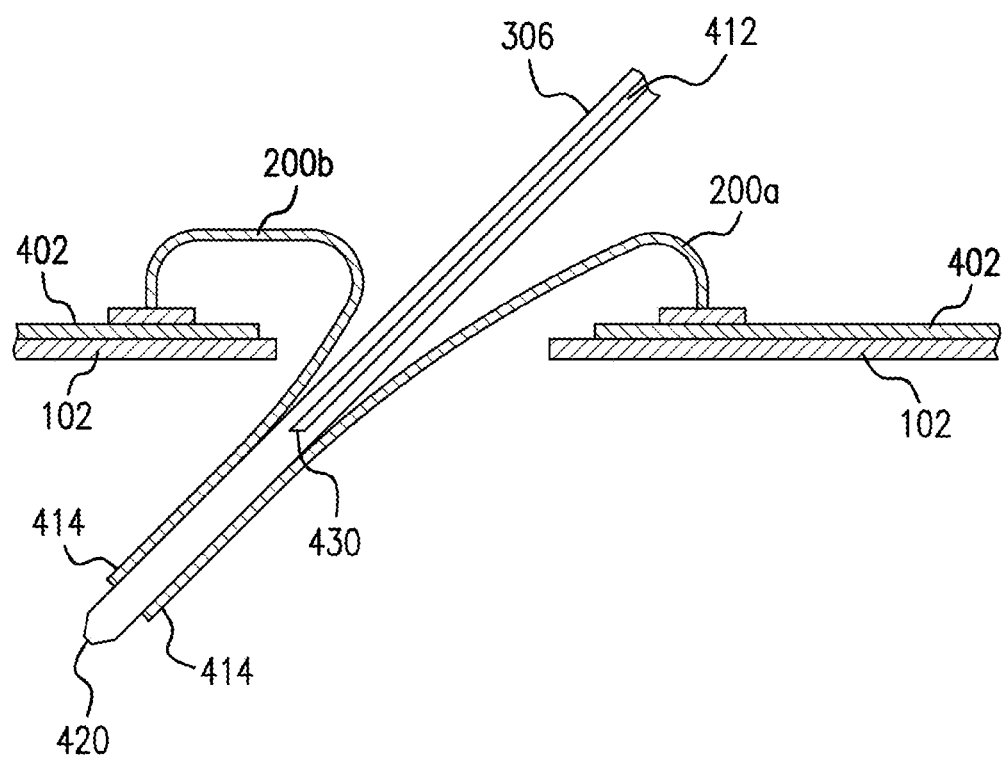
FIG. 4D is an exemplary illustration of a cross-section view of a combined infusion set and sensor in an intermediary position between a second position and the third position, in accordance with embodiments of the present invention.

FIG. 4D is an exemplary illustration of a cross-section view of a combined infusion set and sensor in an intermediary position between a second position and the third position, in accordance with embodiments of the present invention. In the second position the combined infusion set and sensors have been inserted into the desired insertion depth within the subject. In many embodiments, the amount of sensor slack contributes to ensuring the combined infusion set and sensors are placed at the desired insertion depth. Accordingly, in some embodiments, upon achieving the second position the sensor slack has been entirely eliminated. In other embodiments, upon achieving the second position substantially all of the sensor slack has been eliminated.

In some embodiments elimination of the sensor slack works in conjunction with a defined insertion depth of the sharp. In other embodiments, the insertion depth of the sharp is primarily responsible for defining the insertion depth of the combined infusion set and the sensor. Note that while FIGS. 4B-4D are illustrations of the combined infusion set and sensor being inserted at an angle, this does not preclude performing insertion of the infusion set and sensor substantially perpendicular to the skin of the subject. Alternatively, these embodiments can be viewed as vertical insertion, rather than angled insertion. It may be preferable to use angled insertion, as shown in FIGS. 4B-4D, rather than vertical insertion because angled insertion places a greater amount of sensor area under the skin while minimizing insertion depth. After placement of the combined infusion set and sensor at the desired insertion depth, the sharp is withdrawn from the cannula hollow, as shown in FIG. 4D.

The embodiments shown in FIGS. 4A-4D are intended to be construed as exemplary rather than limiting. This disclosure should be construed as encompassing the various combinations of features discussed with the various embodiments.

Figure 5A:
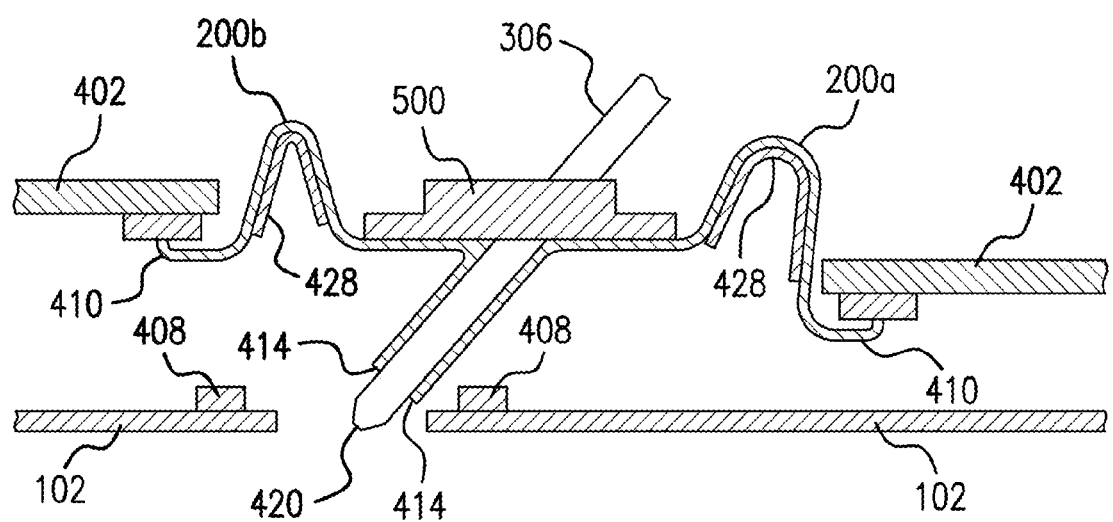
FIGS. 5A and 5B include exemplary illustrations of a combined infusion set and sensor that further includes a cannula hub, in accordance with embodiments of the present invention.
Figure 5B:
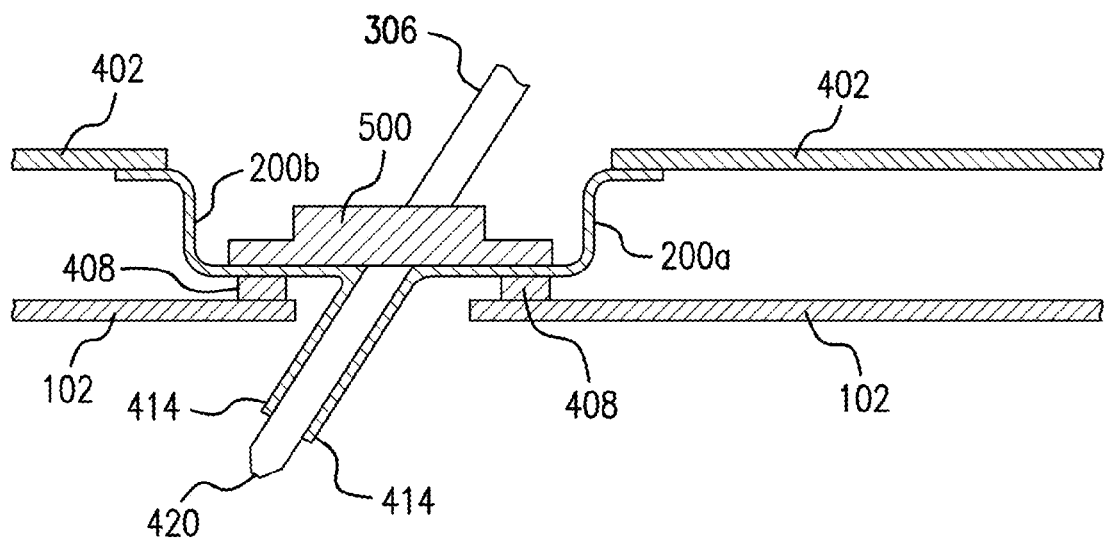

FIGS. 5A and 5B include exemplary illustrations of a combined infusion set and sensor that further includes a cannula hub, in accordance with embodiments of the present invention. The cannula hub is configured to retain or hold the cannula during the insertion process and additionally enables sealing around the through hole.

Figure 6A:
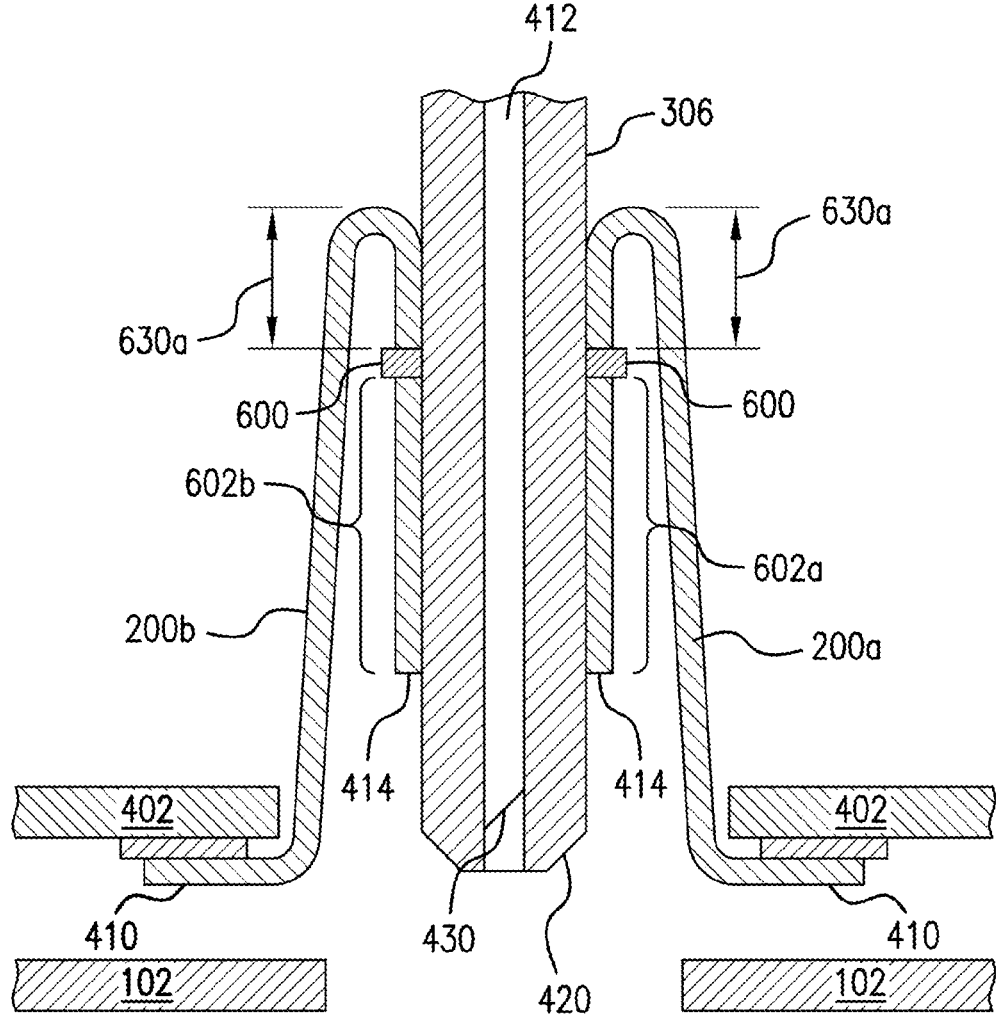
FIGS. 6A and 6B are exemplary illustrations of an alternative embodiment of a combined infusion set and sensor where completion of the insertion process does not result in elimination of sensor slack, in accordance with embodiments of the present invention.
Figure 6B:
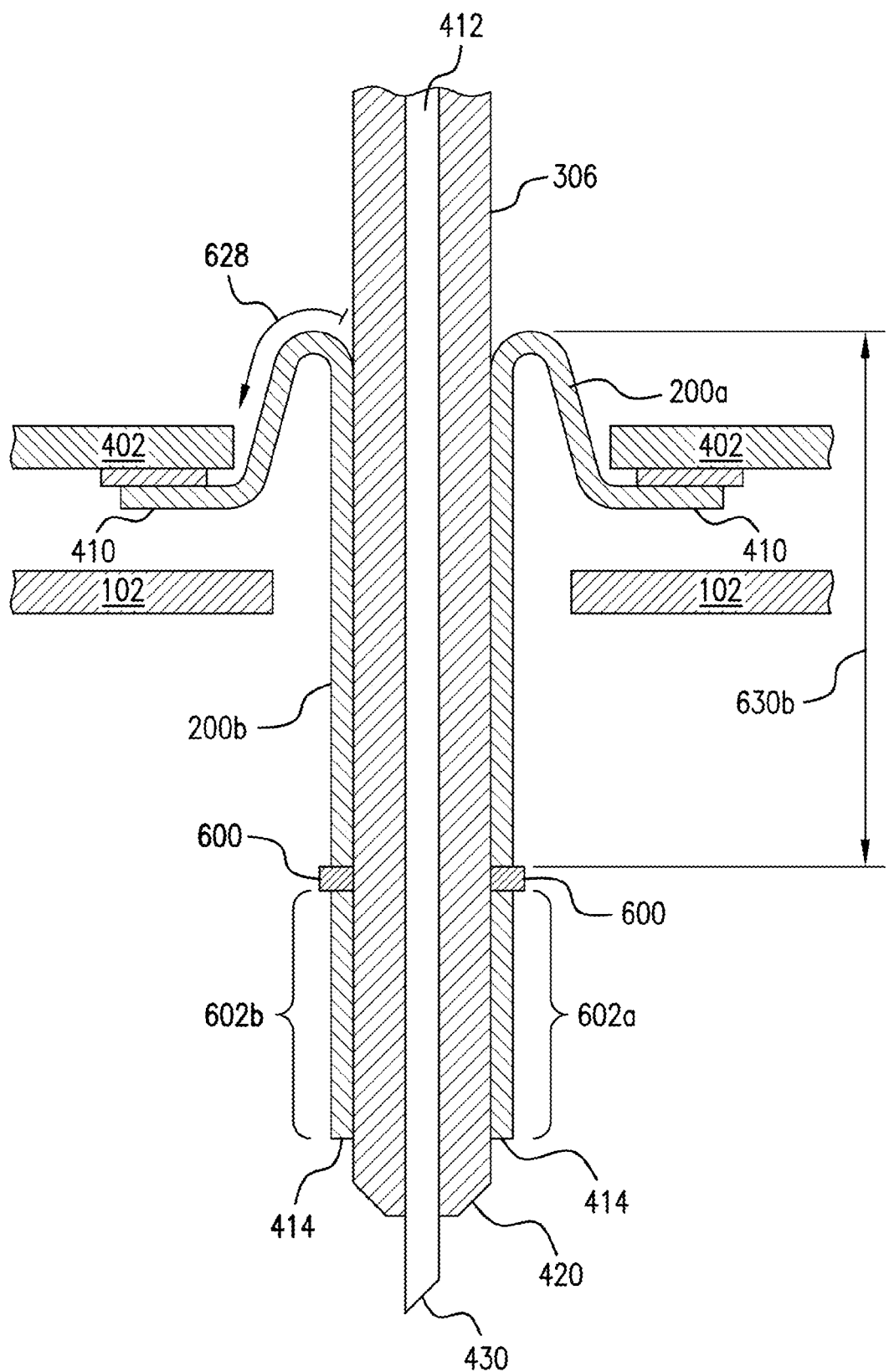

FIGS. 6A and 6B are exemplary illustrations of an alternative embodiment of a combined infusion set and sensor where completion of the insertion process does not result in elimination of sensor slack, in accordance with embodiments of the present invention. As was previously discussed, in some embodiments during the insertion process the sensor is placed or unfurled into a channel within the cannula 306.

In FIGS. 6A and 6B the sensor 200a/200b is secured to the cannula 306 at a second location 600. In some embodiments the sensor 200a/200b is secured to the cannula using mechanical techniques such as, but not limited to staking, bonding or an interference fit within a channel or void formed in the cannula. Being secured at both the second location 600 and the distal end of the sensor 200a/200b, portions 602a and 602 can also be referred to as secured portions 602a and 602b. In some embodiments one or more of the secured portions 602a/602b are pre-installed or pre-positioned within a channel formed in the cannula 306. Accordingly, In FIG. 6A, the cannula, sensor and sharp are in a first position prior to the insertion process and the second location 600 defines a length of double back 630a.

FIG. 6B is an illustration of the cannula, sensor and sharp in a second position, the sharp 412 having reached a desired insertion depth. Note that after the insertion process the length of double back 630b has increased relative to length of double back 630a (FIG. 6A). Additionally note that FIGS. 6A and 6B illustrate an embodiment where there is some sensor slack 628 remaining in sensors 200a and 200b after the insertion process.

The embodiments discussed above are intended to be exemplary. For example, while many of the embodiments are related to sensing using two conductors, other embodiments can be related to generic subdermal sensing using a single conductor or a plurality of conductors to enable sensing or detection of analytes or compounds such as, but not limited to lactate, ketones, oxygen, glucose, reactive oxygen species and the like. Additionally, while many of the embodiments shown in the accompanying figures include a single aperture, various other embodiments can include multiple apertures, where creation of each aperture results in an electrical short circuit. Furthermore, the circular apertures shown in the accompanying figures should not be construed as limiting. Apertures can be formed in various shapes, sizes and at angles other than perpendicular to the sensor such as oblique or acute angles.

In many embodiments, additional features or elements can be included or added to the exemplary features described above. Alternatively, in other embodiments, fewer features or elements can be included or removed from the exemplary features described above. In still other embodiments, where possible, combination of elements or features discussed or disclosed incongruously may be combined together in a single embodiment rather than discreetly as in the exemplary discussion.

Accordingly, while the description above refers to particular embodiments of the invention, it will be understood that many modifications or combinations of the disclosed embodiments may be made without departing from the spirit thereof. The presently disclosed embodiments are therefore to be considered in all respects as illustrative and not restrictive.

The invention claimed is:

1. An infusion set and sensor assembly to be delivered within a subject, comprising:
    a cannula being terminated at a cannula opening;
    a sharp being at least partially within the cannula; and
    a sensor having a proximal end and a distal end, the proximal end being held in a fixed location, the distal end being retained with a portion of the cannula, the sensor further having sensor slack that is defined as an amount of the sensor doubling back upon itself;

wherein transitioning the sharp from a first position to a second position simultaneously inserts the cannula and sensor to a desired insertion depth within the subject via a single point of insertion, and during the transition between the first position and the second position, there is a change in an amount of sensor slack that places the sensor within a channel and reinforces the cannula to prevent bending or kinking of the cannula.

2. The infusion set and sensor assembly of claim 1, wherein when in the first position, the cannula, the sharp, the sensor and the sensor slack are contained within a housing.

3. The infusion set and sensor assembly of claim 1, wherein the proximal end of the sensor is affixed to a circuit board within a housing.

4. The infusion set and sensor assembly of claim 3, wherein a moisture impermeable seal is applied to affix the proximal end of the sensor to the circuit board.

5. The infusion set and sensor assembly of claim 1, wherein the change in the amount of sensor slack defines the insertion depth of the cannula and sensor.

6. The infusion set and sensor assembly of claim 1, wherein an insertion depth of the sharp defines the insertion depth of the cannula and sensor.

7. The infusion set and sensor assembly claim 1, wherein the change in the amount of sensor slack partially defines the insertion depth of the cannula and sensor.

\* \* \* \* \*